United States Patent [19]

Rutzen et al.

[11] Patent Number: 4,492,802

[45] Date of Patent: Jan. 8, 1985

[54] PROCESS FOR MANUFACTURE OF QUATERNARY AMMONIUM COMPOUNDS

[75] Inventors: Horst Rutzen, Langenfeld; Peter Nikolaus, Hilden; Martin Bischoff, Gelsenkirchen; Rudolf Lehmann, Neuss, all of Fed. Rep. of Germany

[73] Assignees: Henkel Kommanditgesellschaft auf Aktien, Dusseldorf; Degussa Aktiengesellschaft, Frankfurt am Main, both of Fed. Rep. of Germany

[21] Appl. No.: 369,760

[22] Filed: Apr. 19, 1982

[30] Foreign Application Priority Data

Apr. 23, 1981 [DE] Fed. Rep. of Germany ....... 3116087

[51] Int. Cl.$^3$ ............................................. C07C 89/02
[52] U.S. Cl. .................... 564/292; 564/295; 564/294; 564/296; 564/285
[58] Field of Search ............... 564/292, 294, 293, 295, 564/296, 285

[56] References Cited

U.S. PATENT DOCUMENTS

| | | | |
|---|---|---|---|
| 3,373,201 | 3/1968 | Van Eygen | 564/293 |
| 3,624,082 | 11/1971 | Skokie et al. | 564/292 |
| 3,755,334 | 8/1973 | Sommer | 564/292 |
| 3,872,170 | 3/1975 | Bosche et al. | 564/293 |

OTHER PUBLICATIONS

Schoenfeldt "Surface Active Ethylene Oxide Adducts," pp. 669–676 (1970).

J. Goerdeler in Houben–Weyl, Methoden der Organischer Chemie, 4th Edition, vol. 11/12, pp. 592 et seq.

*Primary Examiner*—James H. Reamer
*Attorney, Agent, or Firm*—Ernest G. Szoke; Henry E. Millson, Jr.; Mark A. Greenfield

[57] ABSTRACT

Process for the manufacture of quaternary ammonium compounds by reacting a compound having a terminal epoxide troup with a salt of a tertiary amine in the presence of a quaternary ammonium compound as catalyst.

10 Claims, No Drawings

PROCESS FOR MANUFACTURE OF QUATERNARY AMMONIUM COMPOUNDS

BACKGROUND OF THE INVENTION

The manufacture of quaternary ammonium compounds is generally carried out by alkylating a tertiary amine to the quaternary stage. The alkylating agent is usually an ester of a strong mineral acid, especially sulfuric or sulfonic acid esters, or an alkyl halide, for reaction with the tertiary amine. Occasionally, other esters are employed. Another known method for alkylating tertiary amines is by reacting alkylene oxides with tertiary amines in the presence of water. A number of other procedures can also be employed to manufacture quaternary ammonium compounds from readily available tertiary amines. See, e.g., J. Goerdeler in Houben-Weyl, Methoden der organischer Chemie, 4th Edition, Vol. 11/12, page 592 et seg.

Quaternary ammonium compounds with one or more long, aliphatic radicals, or one long aliphatic radical and one aromatic radical exhibit antimicrobial as well as textile softening and antistatic properties, and they are used extensively for these purposes. Such compounds are obtained either by alkylating tertiary amines having long aliphatic groups and/or aromatic groups, or by alkylating with alkylating agents that contain long aliphatic or aromatic groups. Obviously, the tertiary amine as well as the alkylating agent can each contain long aliphatic and/or aromatic groups.

Disadvantages of these known processes for the manufacture of quaternary ammonium compounds include the fact that usually pressure must be used, and occasionally solvents are also required. In addition, the yield is usually disappointing.

DETAILED DESCRIPTION OF THE INVENTON

A process has now been discovered for the preparation of quaternary ammonium compounds using terminal epoxides and tertiary amines which does not suffer from the disadvantages of the above prior art processes.

The present process is carried out by reacting a compound containing a terminal epoxide group with a salt of a tertiary amine in the presence of a quaternary ammonium compound which acts as a catalyst for the reaction.

The salt of the tertiary amine which is to be reacted with the epoxide compound is preferably dissolved in water prior to use. The aqueous solution of the tertiary amine salt can be prepared either by dissolving the salt to be used in sufficient amounts of water, or by forming the salt by adding an equivalent amount of acid to an aqueous solution of the tertiary amine. The tertiary amine salt solution is then reacted with the epoxide compound in the presence of a quaternary ammonium compound as a catalyst. Useful reaction temperatures are in the range of from about 40° to about 100° C.; with a temperature in the range of about 80° to about 95° C. being preferred.

The amount of catalyst to be added to the aqueous solution is from about 0.5 to about 10 wt. %, based on the theoretical weight of the end product. The optimum quantity of catalyst is somewhat dependent on the choice of the epoxide and the amine salt reactants, and the optimum weight of catalyst can be readily determined by simple preliminary experiments.

The epoxide compound and the tertiary amine salt are preferably reacted in an approximately equivalent relationship, and more preferably in a relationship of 1 equivalent of epoxide compound to about 1.1 equivalent of tertiary amine salt.

Terminal epoxy compounds for use in the practice of the invention are straight or branched chain 1,2-epoxyalkanes, which are conveniently obtained from the appropriate 1,2-monolefin or olefin mixture by known methods, such as by the polymerization of ethylene using organic aluminum compounds as catalysts, or by thermal cracking of paraffin hydrocarbons. Examples of preferred 1,2-epoxyalkanes are 1,2-epoxyhexane, 1,2-epoxydecane, 1,2-epoxydodecane, 1,2-epoxytetradecane, 1,2-epoxyhexadecane, and 1,2-epoxyoctadecane. Also suitable are epoxide mixtures such as $C_{12/14}$-1,2-epoxide with about 70 weight percent $C_{12}$- and about 30 weight percent $C_{14}$-epoxyalkane or $C_{16/18}$-1,2-epoxide with about 40 weight percent $C_{16}$- and about 60 weight percent $C_{18}$-epoxyalkane. In addition, a diepoxyalkane having 8 to 20 carbon atoms and two terminal epoxy groups can also be used, such as 1,2-7,8-diepoxyoctane, 1,2-9,10-diepoxydecane, and similar compounds. Also, mono- or diglycide ethers such as hexadecyl monoglycide ether and 1,4-butanediol-diglycide ether are useful epoxide compounds having terminal epoxide groups. The preferred epoxide compounds that can be employed are either (a) those of the general formula:

wherein $R^1$ is either straight or branched chain aliphatic hydrocarbon group having 1 to 21 carbon atoms, preferably 4 to 16 carbon atoms, or a group of the general formula:

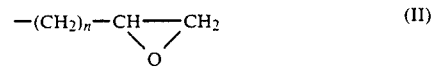

wherein n is an integer of from 4 to 16; or (b) glycide ethers of the general formula:

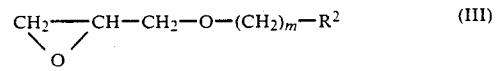

wherein m is an integer of from 1 to 10, and $R^2$ is hydrogen, or an aliphatic straight or branched chain hydrocarbon group having from 1 to 24 carbon atoms, or a group of the formula:

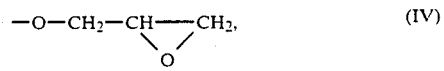

Tertiary amines which are suitable in the form of a salt as reactants with the epoxy compounds used in the process of the invention are the more strongly basic tertiary amines, e.g. those having one or more straight or branched chain alkyl, hydroxyalkyl, or aralkyl (e.g. benzyl, phenylethyl, etc.) groups, or an N-heterocyclic group containing the nitrogen atom of the tertiary amine in the ring structure, wherein such groups contain less than 10 carbon atoms, and wherein the tertiary amine can optionally contain a $C_{10}$ to $C_{20}$ straight or branched chain alkyl or alkenyl group. Examples of such tertiary amines include the trialkylamine, e.g. trimethylamine, triethylamine, tributylamine, dimethylhexylamine, dimethyllaurylamine; the dialkylaralkylamines, e.g. dimethylbenzylamine; tertiary amines containing one or more hydroxyalkyl groups, e.g. dimethylethanolamine, dimethylpropanolamine, N-β-hydroxydecyl-N-βhydroxyethyl-N-methylamine, N-βhydroxyhexadecyl-N-β-hydroxyethyl-N-methylamine, methyldiethanolamine, dimethylaminopropanediol; tertiary diamines such as tetramethylethylenediamine, or tetramethylpropylenediamine-1,3; and, additionally, heterocyclic tertiary amines having the nitrogen atom in the ring structure, e.g. pyridine, picoline, pipecoline, N-methylpiperidine, N-methylpyrrolidine, quinuclidine, etc.

For the acid component of the amine salt, the following inorganic acids are suitable: hydrochloric acid, sulfuric acid, nitric acid, phosphoric acid, hydrobromic acid, hydriodic acid, hydrofluoric acid, boric acid, carbonic acid, or acid salts such as sodium hydrogen sulfate, or sodium hydrogen phosphate. In addition, the acid component can also be one or more organic acids, such as formic acid, acetic acid, succinic acid, benzoic acid, phosphonic acid, phosphoric acid, toluene sulfonic acid, amidosulfonic acid, or an alkyl sulfuric acid. Amphoteric compounds such as dimethylaminoacetic acid can also be used.

Specific examples of amine salts that can be used in the practice of the invention include the hydrocloride or the hydroiodide of trimethylamine, the hydrochloride or the hydrofluoride of dimethylethanolamine, the hydrochloride or the orthoborate of N,N-dimethyl-1-aminopropandiol-2,3, the hydrocloride of N-β-hydroxydodecyl-N-β-hydroxyethyl-N-methylamine, the hydrochloride of N-β-hydroxyhexadecyl-N-β-hydroxyethyl-N-methylamine, the hydrochloride and the formate of tetramethylpropylenediamine-1,3.

Suitable catalysts for use in the present process are quaternary ammonium salts known as phase transfer catalysts, such as tetramethylammonium chloride, methyltrioctyl ammonium chloride, tetrabutylammonium hydrogen sulfate, and the commercially available, typical textile softeners such as dimethylditallow alkyl ammonium chloride, dimethyldistearyl ammonium chloride ("Präpagen WK", Hoechst). The last two compounds are preferred. However, the reaction products produced by the present process are themselves excellent catalysts. Therefore, the reaction product of a prior reaction carried out in accordance with the process of the invention can be used as the catalyst for subsequent reactions. In this process, the catalyst does not have to be separated from the end-product because the catalyst and the reaction product are the same, and neither the catalyst nor the reaction product contains any foreign quaternary ammonium compounds. Such a process, therefore, is the most preferred. However, even in instances where the catalyst and the end-product are not identical, the catalyst does not as a rule interfere with the utility of the end-product, which is a special advantage of the present process. Additionally, poly quaternary compounds obtained by reacting ditertiary amines with diepoxides, or quaternary ammonium compounds on a polymeric matrix, such as the known Lewatit MP 5080 (Bayer Co.) ion exchanger, can be used as a catalyst herein.

In a preferred embodiment of the present process, an epoxyalkane of the general Formula I wherein $R^1$ represents an aliphatic hydrocarbon group having 4 to 16 carbon atoms is reacted with the salt of a tertiary amine and a strong acid in the presence of dimethyldi-($C_{12}$-to $C_{16}$-alkyl- or alkenyl-)ammonium chloride as catalyst.

The process of the invention differs from present state-of-the-art processes in that it does not require pressures in excess of atmospheric, and the reaction takes place at relatively low reaction temperatures and short reaction times. In addition, good yields and end-products of high purity are obtained.

The reaction products of the present process are useful as textile softeners, anti-static agents, and/or as antibacterial agents for application to surfaces to be disinfected such as containers used in the food industry. Particularly useful antibacterial products can be obtained from the process of the invention by either (a) reacting an epoxy compound (with or without an ether linkage) having from 10 to 20 carbon atoms with a salt of a tertiary amine having one or more alkyl, hydroxyalkyl or aralkyl groups wherein each group contains fewer than 10 carbon atoms or (b) reacting an epoxy compound (with or without an ether linkage) having fewer than 10 carbon atoms with a tertiary amine containing a $C_{10}$ to $C_{20}$ alkyl or alkenyl group.

Quaternary ammonium compounds having excellent antistatic and/or textile softening properties can be obtained from the process of the invention by reacting an epoxy compound (with or without an ether group) having at least 6 carbon atoms with a tertiary amine having a $C_{10}$ to $C_{20}$ alkyl or alkenyl group. It has been found that as the number and chain length of the long chain alkyl or alkenyl group increases, the reaction products exhibit gradually increasing textile softening and antistatic properties. Accordingly, the most preferred compounds for these utilities are those formed by the reaction between a tertiary amine that contains a $C_{10}$ to $C_{20}$ alkyl or alkenyl group with an epoxy compound (with or without an ether linkage) having 10 to 20 carbon atoms to produce a quaternary ammonium compound having a $C_{10}$–$C_{20}$ alkyl or alkenyl group and a $C_{10}$–$C_{20}$ hydroxyalkyl or hydroxyalkylether group.

The use of the above products as textile softeners can be in liquid products such as liquids for the after treatment of clean laundry. Such liquids may contain, in addition to one or more of the above products, carrier substances, solvents, diluents, emulsifiers, coloring agents, perfumes, preservatives, viscosity modifiers, thickening agents, and/or other commonly used additives.

An example of a composition useful as a laundry aftertreatment is as follows:

2–80 wt. % of a quaternary ammonium compound prepared by the process of the invention.

20–98 wt. % of carriers, solvents and/or diluents

0–20 wt. % emulsifier

0–3 wt. % preservative

0–5 wt. % perfume

0–1 wt. % coloring agent

Also, the quaternary ammonium compounds produced by the process of the invention can be added to detergent formulations which contain at least one laundry-active compound to produce a softening effect on the laundry. Such detergent formulations are usually based on formulations containing nonionic surfactants. Furthermore, the products of the invention can be applied to textile surfaces as an aid in tumbling.

The invention will be better understood from the following examples which are given for illustration purposes only and not to limit the invention.

EXAMPLE 1

This example describes the preparation of 2-hydroxyhexadecyltrimethylammonium chloride. The % figures represent weight percent.

In a 2 liter three neck flask, 148.8 g (1.1 mole) of 43.7% aqueous trimethylamine solution was diluted with 891 g of water, and with stirring and outside cooling with cold water, 98.6 g (1.0 mole) of 37% hydrochloric acid was added dropwise. 247.6 g (1.0 mole) of distilled, techn. 1,2-epoxyhexadecane (epoxide number 6.46), and 7.0 g of 75% dimethyldistearyl ammonium chloride (10% water, 15% isopropyl alcohol) were added to the flask. While stirring for 5 hours, the resulting reaction mixture was maintained at 80° C. The pH value of the reaction mixture was at 12.2 after 5 hours. After 1.5 hours reaction time the solution became clear.

To 300 g of the reaction mixture, 200 ml of toluene and 200 ml of cyclohexane were added using a water bath, and then the aqueous layer was removed by means of a water separator. The solvent was then distilled off using a water aspirator. The solid residue (74.4 g) was recrystallized using a 75 g butanol/water mixture (6% water). The yield was 71.0 g; which is a yield of 98.1% of theory. The melting point of the purified product was 225°–226° C. Analysis yielded the following data:

|  | OH Number | % N | % Cl |
|---|---|---|---|
| found | 167.7 | 4.17 | 10.50 |
| calculated | 166.9 | 4.17 | 10.55 |

Under otherwise identical conditions, practically no conversion took place when dimethyldistearylammonium chloride was omitted from the reaction mixture.

EXAMPLE 2

This example describes the manufacturer of 2-1-hydroxyhexyltrimethylammonium chloride.

In a process similar to that of Example 1, 224.4 g (1.0 mole) of 57% aqueous hydriodic acid was added to 148.4 g (1.1 mole) of 43.7% aqueous trimethylamine solution diluted with 768 g water. The pH of the solution was 8.2. After adding 103.9 g (1.0 mole) of distilled, techn. 1,2-epoxyhexane (epoxide number 15.41) and 3.5 g of 75% dimethyldistearyl ammonium chloride (10% water, 15% isopropyl alcohol), the resulting mixture was heated to 80° C. and stirred for 5 hours. After 10 minutes, a clear solution was obtained. After 5 hours, the pH was 10.4.

300 g of the reaction mixture was dewatered by the procedure disclosed in Example 1. The crude residue weighed 74.6 g. The crude residue was dissolved in butanone, and precipitated with ethyl acetate. The yield was 95.9% of the theoretical value. The purified product had a melting point of 90°–92° C., as given in the literature. Analysis data:

|  | OH Number | % C | % H | % N | % O |
|---|---|---|---|---|---|
| found | 192.9 | 37.3 | 7.72 | 4.64 | 5.72 |
| calculated | 195.4 | 37.6 | 7.72 | 4.88 | 5.57 |

EXAMPLE 3

This example describes the manufacture of 2-hydroxyhexadecyl-2-hydoxyethyldimethyl ammonium chloride.

The process of this example was carried out according to the process of Example 1. The reaction mixture consisted of the following compounds:

- 49.0 g (0.55 mole) of dimethylethanolamine
- 49.3 g (0.5 mole) of 37% hydrochloric acid
- 498.6 g water
- 132.0 g (0.5 mole) of techn. 1,2-epoxyhexadecane (epoxide number 6.06)
- 3.5 g of 75% dimethyldistearyl ammonium chloride (10% water, 15% isopropyl alcohol)

The conversion took place after 6 hours at 95° C. Toluene/cyclohexane/isopropyl alcohol was used for removing water from the reaction mixture. After recrystallizing the crude reaction product from butanone (melting point 225° C. with decomposition), the yield of purified product was 92.5% of theory.

EXAMPLE 4

(a) The process of Example 1 was carried out with the following reaction components:

- 74.4 g (0.55 mole) of 43.7% trimethylamine solution
- 47.9 g (0.5 mole) of 37% hydrochloric acid
- 456.3 g water
- 127.0 g (0.5 mole) of techn. 1,2-epoxyhexadecane
- 3.7 g of 75% dimethyldistearyl ammonium chloride (b) 14 g of the reaction mixture prepared in (a) above, which had been adjusted to pH 7 with diluted hydrochloric acid, was used as the catalyst for a further process employing the same reaction components as were used in (a) above, except that the dimethyldistearly ammonium chloride was omitted. The same reaction product and yield of reaction product as was obtained in Example 1 was obtained by the present process.

(c) 14 g of the reaction mixture containing crude product that was obtained in (b) above was used as catalyst, with the same reaction components as were used in (a) except that no dimethylstearyl ammonium chloride was present in the reaction mixture. Here again, the same product and yield as were obtained in Example 1 were obtained.

EXAMPLE 5

Using the process of Example 1, 66 g (0.55 mole) of N,N-dimethyl-1-aminopropanediol-2,3 were diluted with 154.3 g water, and while cooling, 49.3 g (0.5 mole) of 37% hydrochloric acid was added. The resulting solution had a pH of 9.2. Then 123.8 g (0.5 mole) of distilled 1,2-epoxyhexadecane and 3.5 g of 75% dimethyldistearyl ammonium chloride were added, and the resulting mixture heated to 95° C. with stirring for 3.5 hours. A clear solution was obtained which exhibited microbiostatic and microbiocidal properties toward a number of test bacteria (such as Pseudomonas aerug, Staph. aureus, and E. coli).

EXAMPLE 6

To 127.3 g (0.55 mole) of N-β-hydroxydecyl-N-β-hydroxyethyl-N-methylamine and 160.1 g of water, 49.3 g (0.5 mole) of 37% hydrochloric acid was added with cooling and stirring. The resulting solution had a pH of 8.0. 80.5 g (0.5 mole) of techn. 1,2-epoxydecane(epoxide number 9.93), and 7 g 75% dimethyldistearyl ammonium chloride were added and the process of Example 1 carried out using a temperature of 95° C. An almost homogeneous solution was obtained which exhibited good antimicrobial properties.

EXAMPLE 7

To 157.8 g (0.5 mole) of N-β-hydroxyhexadecyl-N-β-hydroxyethyl-N-methylamine and 173.0 g of water, 49.3 g (0.5 mole) of 37% hydrochloric acid was added. After adding 65.95 g (0.25 mole) of techn. 1,4-butanedioldiglycide ether (epoxide number 12.13, Emser Works) and 7 g of 75% dimethyldistearyl ammonium chloride, the resulting mixture was heated to 95° C. A clear solution was obtained which was stirred for 5 hours.

The purification of the reaction product was carried out according to the procedure described in Example 1.

EXAMPLE 8

This example describes the manufacture of a quaternary ammonium borate salt. 31 g (0.5 mole) of orthoboric acid was gradually added to a mixture of 180 g of water and 60 g (0.55 mole) of N,N-dimethyl-1-aminopropandiol-2,3. The resulting solution has a pH of 10.6. 7 g of 75% dimethyldistearyl ammonium chloride and 98.7 g (0.5 mole) of distilled 1,2-epoxydodecane were added to the solution and the solution stirred for 21 hours at 95° C. The clear solution had an epoxide number of 0.45, and could be further diluted with water without clouding. Water separation was achieved as described in Example 1. After evaporating in a vacuum and recrystallizing from acetone/isopropyl alcohol, there was obtained 40.5 g of an ammonium borate salt which melted with decomposition at 155°–158° C.

EXAMPLE 9

This example describes the manufacture of a betaine.

3.3 g of 75% dimethyldistearyl ammonium chloride and 46.6 g (0.236 mole) of distilled 1,2-epoxydodecane was added to a solution consisting of 24.4 g (0.236 mole) of dimethylaminoacetic acid in 61.4 g water. After stirring for 5.5 hours at 95° C., there was obtained a viscous solution which was then further diluted with 135.6 g of water, and heated for 6 additional hours at 95° C. This solution (pH 7.2) had an epoxide number of 0.12, and an acid number of 14.5. From 100 g of this solution there was obtained, after removing water as in Example 1, and recrystallization from butanone containing 3% water, 25.6 g of a solid substance having a melting poit of 157°–180° C.

EXAMPLE 10

This example describes the manufacturer of a polymeric quaternary compound.

98.6 g (1.0 mole) of 37% hydrochloric acid were stirred with cooling into a mixture consisting of 71.6 g (0.55 mole) of tetramethylpropylenediamine-1,3 and 430.8 g of water. After adding 3.5 g of 75% dimethyldistearyl ammonium chloride and 65.95 g (0.5 moles) of 1,4-butanediol-diglycide ether (epoxide number 12.13; Emser Work Co.), the mixture was stirred for 6 hours at 95° C. The reaction mixture then had an epoxide number of 0.14 and an acid number of 47.5. A small quantity of polymerized glycide ether was filtered off. 300 g of the filtered solution was dewatered as in Example 1. 75 g of a hard, yellow, somewhat hygroscopic substance was obtained.

EXAMPLE 11

This example describes the use of a cationic ion exchanger as the catalyst.

49.3 g (0.5 mole) of 37% hydrochloric acid was added with cooling to 506.9 g water and 49.0 g (0.55 mole) of dimethylethanolamine. The resulting solution had a pH of 8.0. After adding 123.4 g (0.5 mole) of 1,2-epoxyhexadecane (epoxide number 6.48) and 3.5 g Lewatit MP 5080 (Merck Co.), the mixture was stirred for 16 hours at 95° C. The epoxide number was 0.0. and the acid number 1.4.

EXAMPLE 12

This example describes the manufacture of a bisquaternary compound with textile softening properties.

28.8 g (0.25 mole) of 85% orthophosphoric acid was added with cooling to a solution consisting of 35.8 g (0.275 mole) of tetramethylenepropylenediamine-1,3 in 28.8 g of water. There was then added with stirring 145.7 g (0.5 mole) of techn. 1,2-epoxyoctadecane (epoxide number 5.49) and 3.5 g 75% dimethyldistearyl ammonium chloride. After 4.5 hours reaction time at 95° C., the epoxide number decreased to 0. After the addition of 78.7 g ethanol, crystallization of the reaction product occurred while cooling.

EXAMPLE 13

Following the same method as in Example 12, a bisquaternary compound was produced from 35.8 g (0.275 mole) of tetramethylenepropylenediamine-1,3, 29.2 g water, 23,0 g (0.5 mole) of formic acid, 123.8 g (0.5 mole) of distilled 1,2-epoxyhexadecane (epoxide number 6.48), and 3.5 g 75% dimethyldistearyl ammonium chloride. After 5 hours at 95° C., the epoxide number decreased to 0.13.

The quaternary ammonium compound produced by the reaction, which was isolated and purified by the method given in Example 1, exhibited definite textile softening properties.

EXAMPLE 14

This example describes the manufacture of a quaternary ammonium compound using a monoglycide ether.

49.3 g (0.5 mole) of 37% nitric acid were added to 74.4 g (0.55 mole) of 43.7% aqueous trimethylamine solution while cooling with ice water. 178.5 g (0.5 mole) of hexadecylglycide ether (epoxide number 4.47) and 3.5 g of 75% dimethyldistearyl ammonium chloride were then added. After 2 hours at 95° C., the epoxide number was reduced to about 0. A very viscous solution at room temperature was obtained from the reaction mixture.

EXAMPLE 15

95.1 g (0.5 mole) of p-toluene sulfonic acid monohydrate were gradually added to a mixture of 74.4 g (0.55 mole) of trimethylamine solution in 601 g of water. 3.5 g of dimethyldistearyl ammonium chloride (75%) and 98.7 g (0.5 mole) of 1,2-epoxydodecane were added, and the resulting mixture stirred for 5 hours at 80° C. After 1.7 hours a clear solution was obtained. To 300 ml of this solution, 200 ml of toluene, 200 ml cyclohexane, and 100 ml of isopropyl alcohol were added, and water removed from the mixture by means of a water separator. After distilling the solution, there was obtained 81.6 g of crude product. Using 85 g of butanone and 3.4 g of water, the crude product was crystallized three times. The melting point was 180° to 181.5° C.; nitrogen content and OH-number agreed with the theoretical values for trimethyl-β-hydroxydodecylammonium-p-toluene sulfonate.

EXAMPLE 16

49.0 g (0.5 mole) of 98% methansulfonic acid was added to a mixture consisting of 626.9 g water and 49.0 g (0.55 mole) of dimethylethanolamine. Afterwards, 3.5 g of dimethyldistearyl ammonium chloride were added. There was then added with stirring 123.84 g (0.5 mole) of 1,2-epoxyhexadecane (epoxide number 6.46). The resulting mixture was stirred for 14 hours at 95° C. A clear solution was obtained (epoxide number 0.06).

The nitrogen content of the product (melting point 94° C.) thrice recrystallized from ethyl acetate was 3.29% (theoretical value: 3.25%).

EXAMPLE 17

285.05 g of water and 49.3 g (0.5 mole) of 37% hydrochloric acid were added to 61.15 g (0.55 mole) of quinuclidine. 94.0 g of 1,2-epoxydodecane (0.5 mole) and 3.5 g of dimethyldistearyl ammonium chloride (75%), were added, and the resulting mixture heated to 95° C. with stirring. After 15 minutes the epoxide number had decreased to 0.035. The reaction product contained 89.8% of the theoretical value of the quaternary ammonium reaction product.

What is claimed is:

1. A process for the preparation of a quaternary ammonium compound comprising the steps of
   (I) forming an aqueous mixture of
       (a) a compound containing a terminal epoxy group selected from the group consisting of
           (i) a compound of the formula

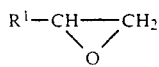             (I)

wherein R¹ is a straight or branched chain aliphatic hydrocarbon group having 4 to 16 carbon atoms or a group of the formula

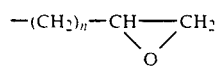             (II)

wherein n is an integer of from 4 to 16, and
           (ii) a compound of the formula

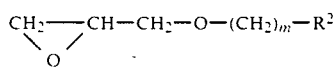             (III)

wherein m is an integer of from 1 to 10, and R² is hydrogen, or a straight or branched chain aliphatic hydrocarbon group having from 1 to 24 carbon atoms, or a group of the formula

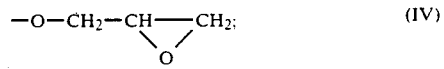             (IV)

(b) a salt of a tertiary amine which contains one or more alkyl, hydroxyalkyl, or aralkyl groups wherein such groups each contain less than 10 carbon atoms, and wherein the tertiary amines can optionally contain a $C_{10}$ to $C_{20}$ straight or branched chain alkyl or alkenyl group; and
       (c) from about 0.5 to about 10% by weight, based on the theoretical weight of the quaternary ammonium compound reaction product, of a quaternary ammonium catalyst and
   (II) heating said aqueous mixture to a temperature in the range of from about 40° to about 100° C. for a period of time sufficient to produce a quaternary ammonium compound from the reaction between compound (a) and compound (b) above.

2. A process in accordance with claim 1 wherein the salt of a tertiary amine I (b) is first formed by dissolving the tertiary amine precursor in water, adding an acid thereto to form an aqueous solution of a salt of the tertiary amine, and the compound containing a terminal epoxy group (I) (a) and the quaternary ammonium catalyst (I) (c) are added to the aqueous salt solution.

3. A process in accordance with claim 1 or 2 wherein the reaction is carried out at normal atmospheric pressure.

4. A process in accordance with claim 3 wherein the reaction temperature is in the range of from about 80° to about 95° C.

5. A process in accordance with claim 1 wherein the epoxy compound (I) (a) and the tertiary amine salt (I) (b) are present in approximately chemically equivalent quantities.

6. A process in accordance with claim 5 wherein the equivalent ratio of epoxy compound (I) (a) to tertiary amine salt (I) (b) is about 1:1.1.

7. A process in accordance with claim 1 wherein the quaternary ammonium catalyst is identical to the quaternary ammonium compound produced by said reaction.

8. A process in accordance with claim 1 wherein the catalyst is dimethyldi($C_{12}$—$C_{16}$ alkyl or alkenyl) ammonium chloride.

9. A process in accordance with claim 1 wherein the epoxy compound (I)(a) contains from 10 to 20 carbon atoms.

10. A process in accordance with claims 1 or 9 wherein the tertiary amine salt (I)(b) contains an alkyl or alkenyl group having from 10 to 20 carbon atoms.

* * * * *